United States Patent [19]
Uchida et al.

[11] Patent Number: 5,844,660
[45] Date of Patent: Dec. 1, 1998

[54] OBJECTIVES REFRACTION MEASURING APPARATUS

[75] Inventors: Saeko Uchida, Okayama; Yasuo Kato; Kunihiko Hara, both of Tokyo, all of Japan

[73] Assignee: Kabushiki Kaisha, Topcon, Tokyo, Japan

[21] Appl. No.: 911,976

[22] Filed: Aug. 15, 1997

[51] Int. Cl.$^6$ .................................................. A61B 3/10
[52] U.S. Cl. ........................... 351/211; 351/205; 351/239
[58] Field of Search .................................. 351/205, 208, 351/211, 213, 214, 221, 222, 237, 239

[56] References Cited

U.S. PATENT DOCUMENTS

5,594,512  1/1997  Yoneda et al. ............................ 351/221

*Primary Examiner*—Huy Mai
*Attorney, Agent, or Firm*—Oppedahl & Larson

[57] ABSTRACT

An objective refraction measurement apparatus includes a separate chart having a pair of charts arranged separately, an optical system for projecting the separate chart to an eye to be examined through a focusing lens and a diaphragm having a pair of through holes arranged corresponding to the separate arrangement of the pair of charts, an operating unit for performing focusing operation to the eye, and a control unit for moving the focusing lens on the basis of the focusing operation along the optical axis direction by the operating unit to obtain the projection images of the pair of charts in the separate chart to the eye in an identical condition or a non-identical condition, thereby to perform a subjective measurement of the eye.

5 Claims, 8 Drawing Sheets

FIG. 11 ns apparatus
OBJECTIVES REFRACTION MEASURING APPARATUS

BACKGROUND OF THE INVENTION

1. Field of the Invention

The present invention relates to an objective refraction measuring apparatus by which the objective measurement of an eye to be examined can be carried out.

2. Description of Related Art

For example, in a conventional objective refraction measuring apparatus for measuring a variety of eye functions such as a visual acuity and an astigmatism of an eye to be examined in an objective manner, generally an alignment/positioning of the eye to be examined is performed by manipulating the operating unit of the objective refraction measuring apparatus by the examining person such as an optometrist while watching an image monitor thereof, and then an optical system thereof is switched among a far-sight measurement condition and a near-sight measurement condition, for the purpose of objective measurement of the eye to be examined.

In this case, a chart image is projected to a fundus of the eye to be examined in the objective measurement, to thereby automatically obtain the objective measurement value such as a refractive power, and thus it is difficult for the person to be examined by himself or herself to perform the subjective measurement.

SUMMARY OF THE INVENTION

In view of the foregoing difficulties, an object of the present invention is to provide an objective refraction measuring apparatus which may perform an objective measurement of an eye to be examined and which has a function that the person to be examined may perform a subjective measurement by himself or herself.

According to the present invention, there is provided an objective refraction measuring apparatus for measuring a refractive power of an eye to be examined in an objective manner, comprising: a separate chart having a pair of chart arranged separately; an optical system for projecting the separate chart to the eye through a focusing lens and a diaphragm having a pair of holes arranged corresponding the pair of charts; moving means for moving the focusing lens along an optical axis direction to perform an focusing operation to the eye; and means for measuring the eye in a subjective manner while the projection images of the pair of charts to the eye are obtained in an identical condition or a non-identical condition by moving the focusing lens by the moving means.

According to the present invention, the diaphragm is interposed in an optical path of the optical system in accordance with the separate chart.

According to the present invention, the pair of holes of the diaphragm have a red slit and a green slit, respectively.

According to the present invention, the moving means moves the focusing lens in accordance with an objective measurement value obtained from an objective measurement such that the separate chart is set to a desired position in relation to a far-sight position of the eye.

According to the present invention, the addition power of the eye is measured by setting the projection images of the pair of charts to the eye to a near-sight position of the eye in accordance with a subjective measurement value obtained from the subjective measurement in a far-sight position of the eye.

According to the present invention, the subjective measurement of the eye can be performed by a person that the eye is examined.

In the optical system of the objective refraction measurement apparatus according to the present invention, the separate chart composed of the pair of charts arranged separately is projected to the eye to be examined through the focusing lens and the diaphragm having the pair of through holes arranged corresponding to the separate arrangement of the pair of charts.

When the person to be examined performs the aligning operation to the eye to be examined, the moving means moves the focusing lens along the optical axis direction on the basis of the aligning operation, so that the projection image of the pair of charts in the separate charts relative to the eye to be examined is brought into the identical condition or the non-identical condition. Thus, the person himself or herself may perform the subjective measurement of his or her eye in the objective refraction measuring apparatus.

In the objective refraction measurement apparatus according to the present invention, the diaphragm having the pair of through holes is interposed into the optical path of the optical system in response to the separate chart composed of the pair of charts arranged separately. Accordingly, when the subjective measurement is carried out by using the separate chart, the diaphragm having the pair of through holes is automatically interposed into the optical path of the optical system, and it is possible for the person himself or herself to quickly execute the subjective measurement in the objective refraction measuring apparatus.

In the objective refraction measuring apparatus according to the present invention, since one of a pair of through holes in the diaphragm is the red slit and the other hole is the green slit, it is possible to perform the subjective measurement by projecting the red and green slit images to the eye of the person to be examined.

DETAILED DESCRIPTION OF THE PREFERRED EMBODIMENTS

An embodiment of the invention will now be described in detail with reference to the accompanying drawings.

Figure 1:
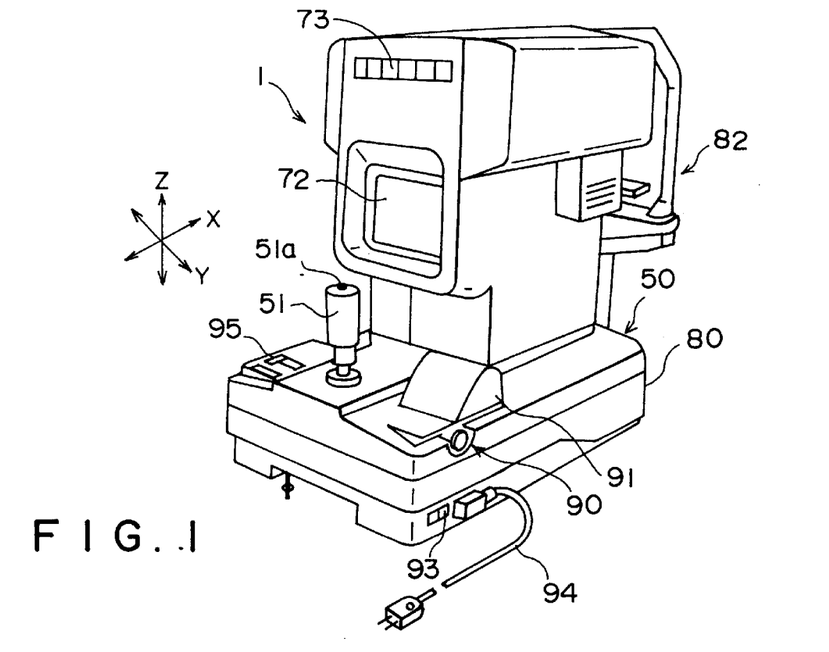
FIG. 1 shows an objective refraction measuring apparatus as viewed from the examiner in accordance with an embodiment of the present invention.
Figure 2:
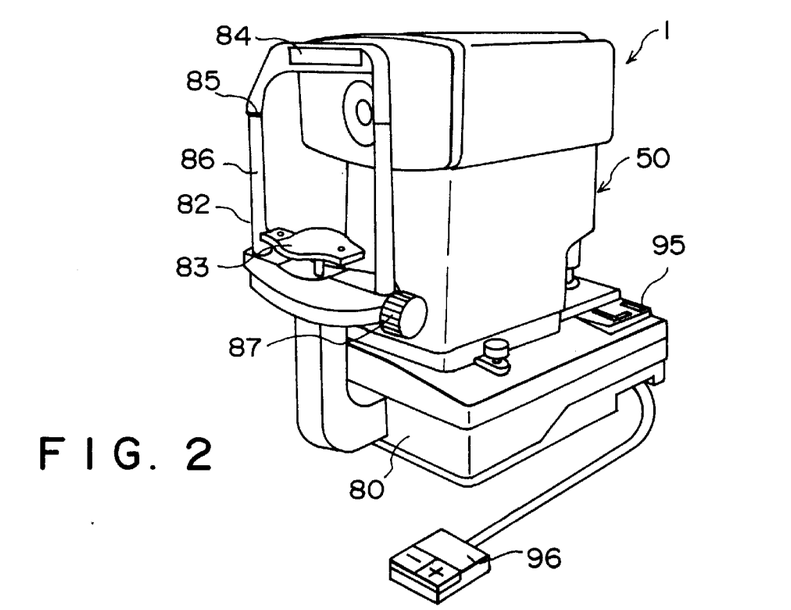
FIG. 2 shows the objective refraction measuring apparatus as viewed from the person to be examined in accordance with the embodiment.

An objective refraction measuring apparatus 1 according to the embodiment of the invention as shown in FIGS. 1 and 2 is provided with a box-shaped apparatus body 50. The apparatus body 50 may be moved on a base table 80 in any direction of X, Y and Z by the operation of an operation handle 51 constituting an operation unit provided with an operation switch 51a.

A jaw receiving base 82 on which jaws of a person to be examined are to be placed is provided on one edge side of the apparatus body 50. The jaw receiving base 82 is provided with a jaw receiver 83, a forehead contact 84, a post 86 having a height mark 85, a jaw receiving handle 87 and the like.

Figure 4:
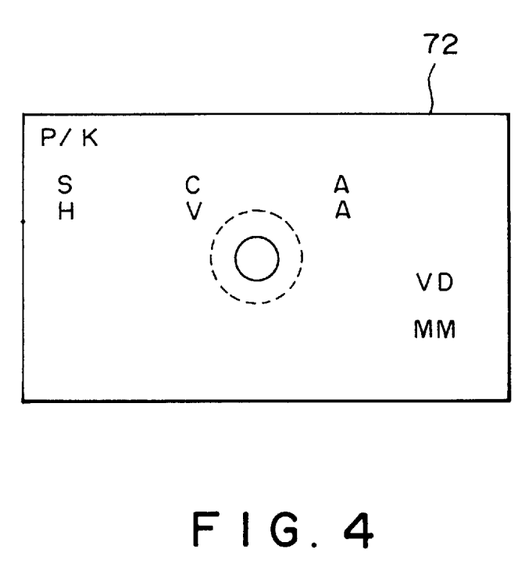
FIG. 4 shows a display example of a display unit of the objective refraction measuring apparatus according to the embodiment.

A display unit 72 for displaying a front eye portion image of the eye E to be examined, a corneal reflective image, various measurement values, a defocus confirmation image or the like, as shown in FIG. 4, is provided in the other edge side of the apparatus body 50.

Figure 3:
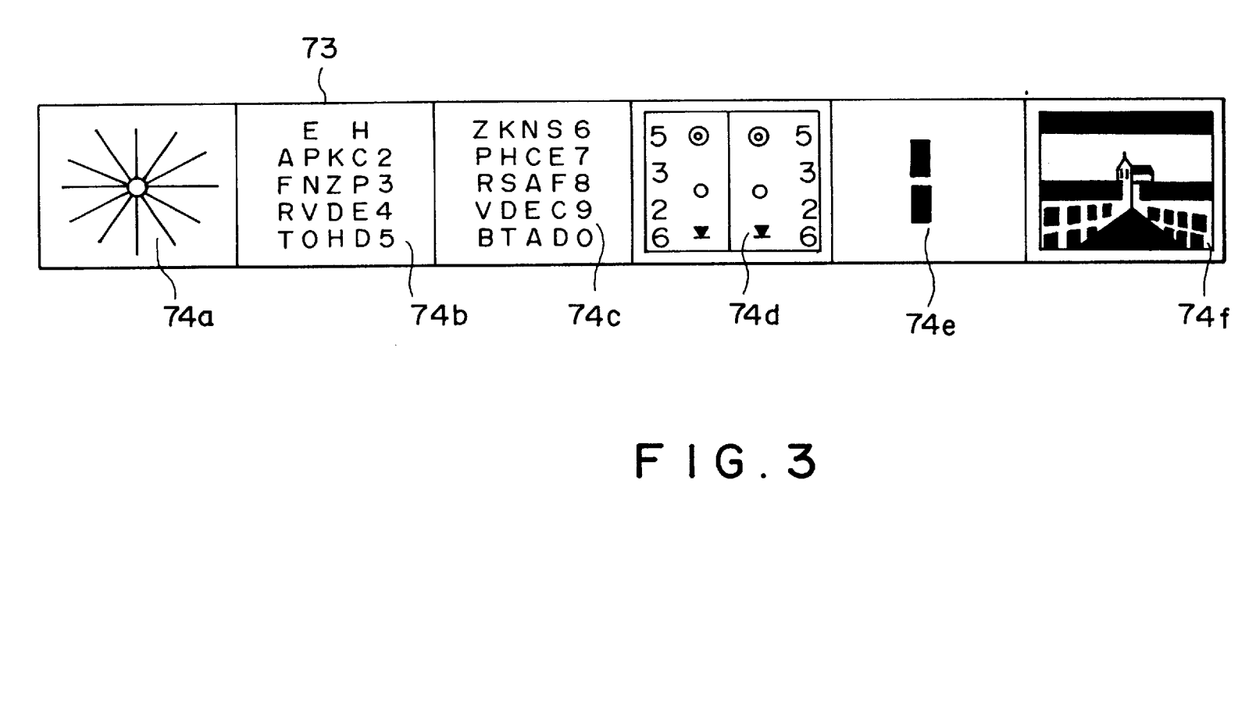
FIG. 3 shows a chart switch panel of the objective refraction measuring apparatus according to the embodiment.

A chart switch panel 73 constituting the operation unit is provided in the upper portion of the display unit 72. As shown in FIG. 3, the chart switch panel 73 has a star burst chart switch 74a, a visual acuity chart switch 74b and 74c, a red/green chart switch 74d, a separate chart switch 74e and a picture chart switch 74f.

As shown in FIG. 1, a printer 90 provided with a printer cover 91 is disposed on the other end side of the apparatus body 50, and a power supply switch 93 and a power supply line 94 are provided. Also, in the other end side of the apparatus body 50, there is provided a switch unit 95 constituting the operation unit which includes a mode selection switch for the subjective measurement or the objective measurement, an addition power measurement switch, a dip switch, an automatic starting switch, a print switch and the like. In the one end side of the apparatus body 50, a mouse 96 constituting the operation unit and may be manipulated by the person to be examined is provided.

An optical arrangement for the apparatus body 50 will now be described with reference to FIGS. 5 and 6. The apparatus body 50 includes an illuminating optical system 400 for illuminating the eye E of the person to be examined and an optical system 500 for irradiating various rays of light into the eye E and receiving a reflective image from the eye E.

The apparatus body 50 including the illuminating optical system 400 and the optical system 500 will now be described in detail.

The optical system 500 of the apparatus body 50 is composed of: a corneal measuring system 1A for measuring a radius of curvature of a cornea C of the eye E to be examined; an objective refractive measuring system 2 for measuring the refractive power of the eye E to be examined in the objective manner; an eye fixation/subjective measuring system 3 for projecting various charts such as a picture chart and a star burst chart which are an eye fixation chart for fixing the eye E to fix a visual axis of the eye to be examined during the measurement, a visual acuity chart and a red/green chart for the subjective measurement, and a separate chart 501 to be described later; and an observation/alignment system 4 for performing the front eye portion observation of the eye E and the alignment between the optical axis of the optical system 500 and the visual axis of the eye E. A portion of the optical path of the observation/alignment system 4 is common with the optical path of the corneal measuring system 1A.

The corneal measuring system 1A has a pattern projection system 10 for projecting an annular pattern to the cornea C to measure the radius of curvature of the cornea C of the eye to be examined and a measuring optical system 11 for measuring a size and a shape of the corneal reflective image of the annular pattern.

The pattern projection system 10 is composed of a pattern plate 101 having an annular opening 100 and an annular light source 102 which is disposed behind the opening 100 and emits corneal measuring light having a wavelength of 930 to 1,000 nm.

The light emitted from the annular light source 102 is projected through the annular opening 100 to the cornea C of the eye E as the projecting light. The projecting light forms a virtual image of the annular opening 100 in the cornea C. The corneal measuring light reflected by the cornea C is incident on the measuring optical system 11 as if the virtual image would be projected.

The measuring optical system 11 is composed of an objective lens 110, a mirror 111 which reflects the visual light having the wavelength of 400 to 700 nm and passes the light in the long wavelength region not shorter than 800 nm including the corneal measuring light (wavelength of 930 to 1,000 nm), a mirror 112 which passes an infrared light having a wavelength of 865 nm and reflects the infrared light having a wavelength of 900 nm or more, a relay lens 113, a diaphragm 114, a mirror 115 which passes a red light having the wavelength of 700 nm but reflects the corneal measuring light, a relay lens 116, a mirror 117 which reflects the infrared light having the wavelength of 865 nm but passes the corneal measuring light and the red light having the wavelength of 700 nm, an imaging lens 118, and a light receiving element 5 such as an area CCD or an imaging tube. A detection signal of the light receiving element 5 is processed by an image processing unit 71 and then is transferred to the display unit 72 under the control of a control unit to be described later.

After the corneal measuring light reflected by the cornea C is collected by the objective lens 110, it passes through the mirror 111. The corneal measuring light is reflected by the mirror 112 and passes through a central portion 114b of the diaphragm 114 through the relay lens 113.

The corneal measuring light is reflected by the mirror 115, introduced to the mirror 117 by the relay lens 116, passes through the mirror 117 and projected on the light receiving element 5 by the imaging lens 118 as a corneal measuring ring pattern.

The refractive power measuring light with the wavelength of 865 nm emitted from a light emitting diode 200 constituting the pattern projection system 20 is received by a condenser lens 201. Thereafter, the light is refracted by a conical prism 202 and is irradiated into a ring pattern 203 which also serves as a defocus confirmation pattern for the refractive power measurement.

The refractive power measuring light passed through the ring pattern 203 is irradiated to a ring diaphragm 207 through a relay lens 204, a mirror 205 and a relay lens 206. The refractive power measuring light is passed through the ring diaphragm 207 and then reflected by a reflective surface 208a of a bored mirror 208.

Thereafter, the refractive power measuring light is reflected by the mirror 209, passes through the mirrors 112 and 111 which are structural elements of the measuring optical system 11 of the corneal measuring system 1A, and projected as an image of the ring pattern 203 on the fundus ER of the eye E to be examined by the objective lens 110.

By the way, the light emitting diode 200 and the ring diaphragm 207 are optically conjugative, and at the same time, the ring diaphragm 207 and the pupil of the eye E to be examined are located in an optically conjugative manner.

In the objective refractive measuring system 2, the light of the ring pattern image reflected by the fundus ER of the eye E to be examined is collected by the objective lens 110. After the collected light (refractive power measuring light) is passed through the mirrors 111 and 112, the light is reflected by the mirror 209 and passes through a diaphragm 210 via an opening portion 208b of the bored mirror 208.

The refractive power measuring light passes through the relay lens 211 via the diaphragm 210, reflected by the mirror 212 which passes the visual light, and irradiated to a filter 215 of an optical unit 219 through a relay lens 213 and a mirror 214.

The filter 215 has a peripheral portion 215b which allows the passage of the refractive power measuring light having the wavelength of 865 nm and a central portion 215a which interrupts the refractive power measuring light. Also, the filter 215 has such characteristics that in the overall region, the corneal measuring light having the wavelength of from 930 to 1,000 nm is not passed but the visual light having the wavelength of from 400 to 700 nm is allowed to pass.

Thus, the refractive power measuring light passes only the peripheral portion 215b of the filter 215, and then passes, through a focusing lens 216, a mirror 217 which reflects the visual light and allows the passage of the refractive power measuring light. After that, the refractive power measuring light is reflected by the mirror 117 of the measuring optical system 11 of the corneal measuring system 1A and then irradiated as the ring pattern image (reflective image of defocus confirmation pattern) on the light receiving element 5 by the lens 118 to convert it into an electric signal.

The focusing lens 216 and the filter 215 are provided integrally in the optical unit 219 together with the light emitting diode 200, the condenser lens 201, the conical prism 202 and the ring pattern 203 of the pattern projection system 20. The optical unit 219 is movable along an optical axis direction and moved along the optical axis direction by a lens driver unit to be described later.

In the objective refractive measuring system 2, the diaphragm 210 is optically conjugative with a position of the pupil of the eye E to be examined with respect to the objective lens 110. Also, the light receiving element 5 is optically conjugative with an intermediate imaging surface of the ring pattern 203 when the eye E is in an emmetropia (refractive power is zero diopter).

The visual light having the wavelength of 400 to 700 nm emitted from the light source 30 of the eye fixation/subjective measuring system 3 is collected by a condenser lens 31 to illuminate the chart board 32.

Figure 5:
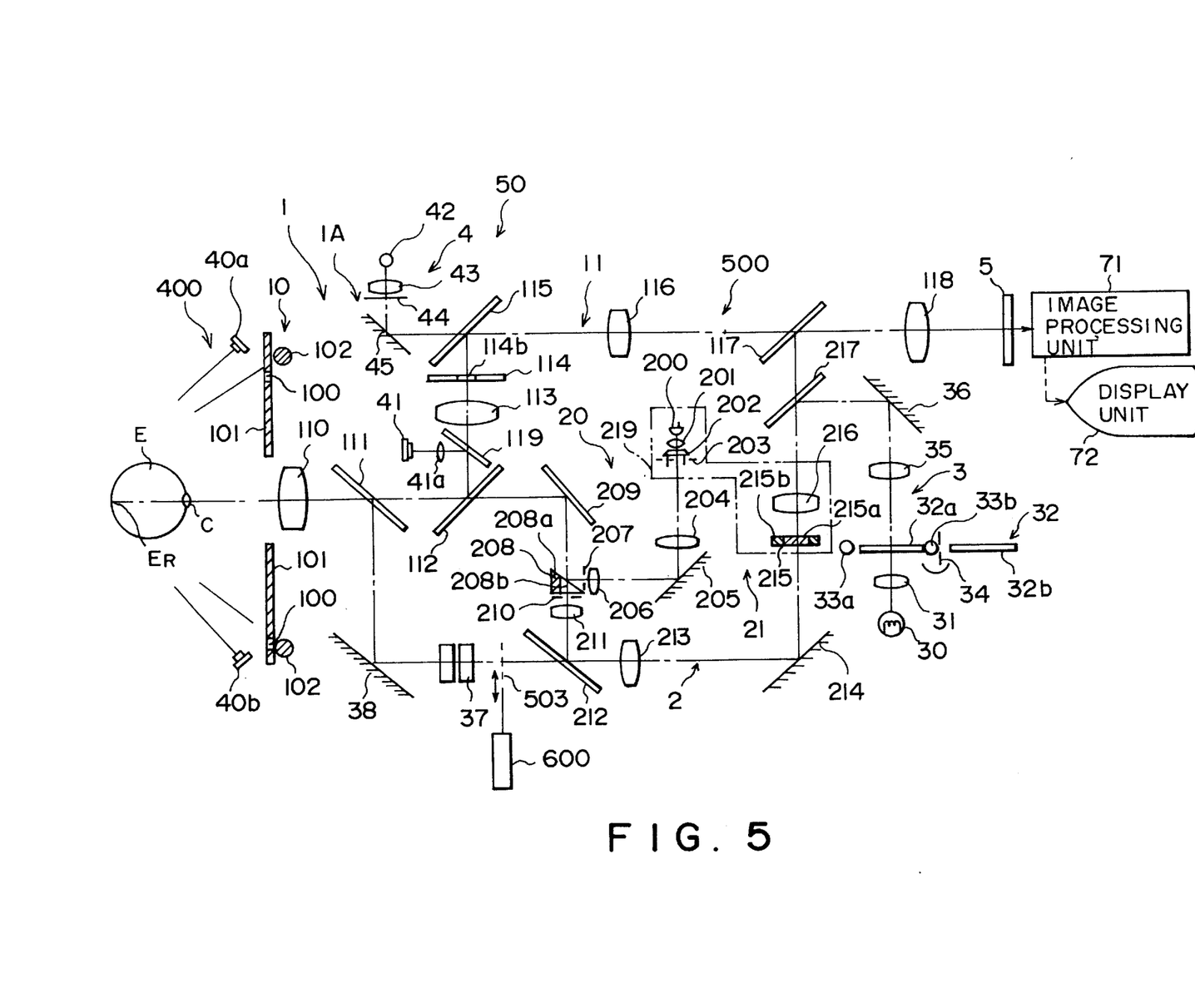
FIG. 5 shows an optical arrangement of the objective refraction measuring apparatus according to the embodiment.

In the chart board 32 (FIG. 5 shows chart boards 32a and 32b), the star burst chart, the visual acuity chart for the subjective inspection, the separate chart 501 and the like are arranged in the circumferential direction. Each chart may be selectively interposed in the optical path of the eye fixation/subjective measuring system 3 by rotating the chart board 32 around an axis 34.

The light passed through the star burst chart, the separate chart or the like passes the projection lens 35, and then is reflected by the mirror 36. Thereafter, the light is reflected by the mirror 217 and merged into the measuring optical system 21 of the objective refractive measuring system 2. Also, the light passes the filter 215 through the focusing lens 216 and is introduced into the mirror 212 through the mirror 214 and the relay lens 213. The light passed through the mirror 212 is further introduced into a variable cross cylinder 37 through a diaphragm 503 having a pair of through holes 503a and 503b corresponding to a pair of separately arranged marks 501a and 501b which constitute the separate chart 501 shown in FIG. 6.

Figure 6:
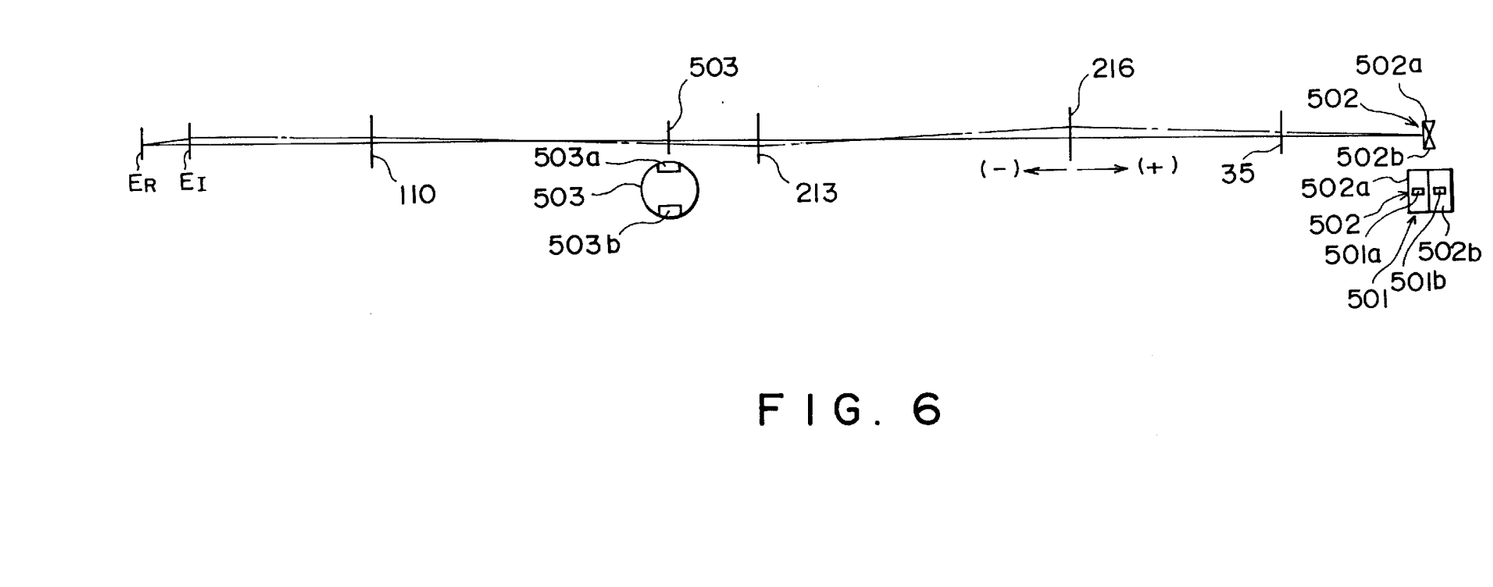
FIG. 6 shows an optical arrangement for projecting the separate charts to the eye in the objective refraction measuring apparatus according to the embodiment.

As shown in FIG. 6, the pair of separately arranged marks 501a and 501b of the separate chart 501 are attached to a central portion of a split prism 502 composed of a pair of prisms 502a and 502b arranged so that their oblique directions are opposite to each other and their oblique angles are the same.

The light passed through the variable cross cylinder 37 is reflected by a mirror 38 and a mirror 111, projected to the eye E to be examined by the objective lens 110 and observed by the eye E to be examined.

The light source 30 of the eye fixation/subjective measuring system 3 and the diaphragm 503 are in the conjugative relation with each other.

A red filter and a green filter are attached to the pair of through holes 503a and 503b of the diaphragm 503, respectively, so that the through hole 503a serves as a red slit and the through hole 503a serves as a green slit. Also, the diaphragm 503 is so arranged as to be interposed in the optical path of the objective refractive power measuring system 2 and to be retracted away from that path by an electromagnetic solenoid 600.

The separate chart 501 and the fundus ER of the eye E to be examined are set in conjugative relation with each other when the eye E is in the emmetropia. The diaphragm 503 and the pupil EI of the eye E to be examined are set in conjugative relation with each other.

A plurality of glare light sources 33a and 33b for emitting the visual light for the glare test are disposed in the vicinity of the chart board 32. The glare light sources 33a and 33b may be disposed near the objective lens 110. Also, for the glare test, instead of providing the glare light sources 33a and 33b, for example, it is possible to use a structure for changing the contrast between the visual acuity chart and the base of the chart board 32.

A plurality of light emitting diodes 40a and 40b for illuminating the front eye portion are arranged outside of the pattern plate 101 of the pattern projection system 10 of the corneal measuring system 1A, so that the infrared light having the wavelength of 900 nm emitted from each of the light emitting diodes 40a and 40b is illuminated into the front eye portion of the eye E to be examined.

After the light reflected at the front eye portion of the eye E to be examined is collected by the objective lens 110, it passes the mirror 111 and is then transmitted along the measuring optical system 11 of the corneal measuring system 1A to be imaged on the light receiving element 5 by the imaging lens 118.

On the other hand, the light from a focusing/positioning light source 41 which emits the infrared light having a wavelength of 900 nm is projected to the cornea C of the eye E to be examined through a relay lens 41a, a half-mirror 119 and the objective lens 110.

The observation/alignment system 4 is disposed in front of the mirror 115 of the measuring optical system 11 of the corneal measuring system 1A. The observation/alignment system 4 has a light emitting diode 42 for emitting a light (scale light) having a wavelength of 700 nm, a collective lens 43 for collecting the scale light from the light emitting diode 42, and a mirror 45 for reflecting the scale light passed through a sighting scale 44 and for emerging the light into the measuring optical system 11.

Figure 9:
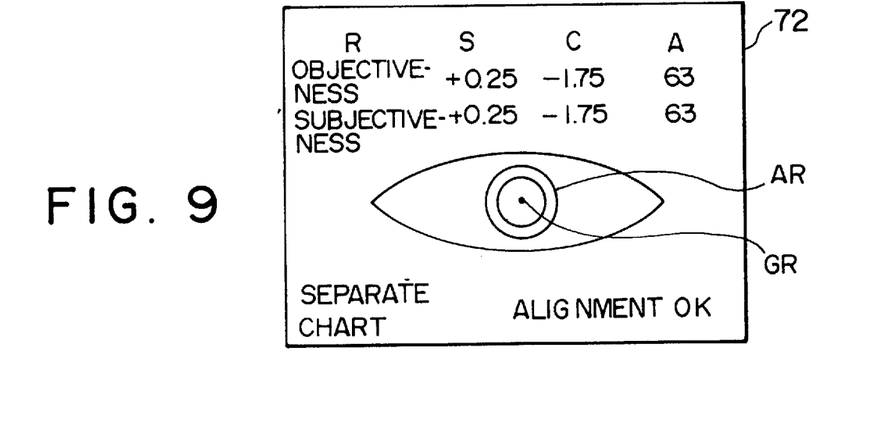
FIG. 9 shows a display example of a display unit of the objective refraction measuring apparatus according to the embodiment.

The scale light which is passed through the sighting scale 44 and reflected by the mirror 45, is projected on the light receiving element 5 through the measuring optical system 11 by the lens 118 after the passage of the mirror 115. Thus, an alignment circle AR is displayed on the display unit 72, as shown in FIG. 9.

Figure 7:
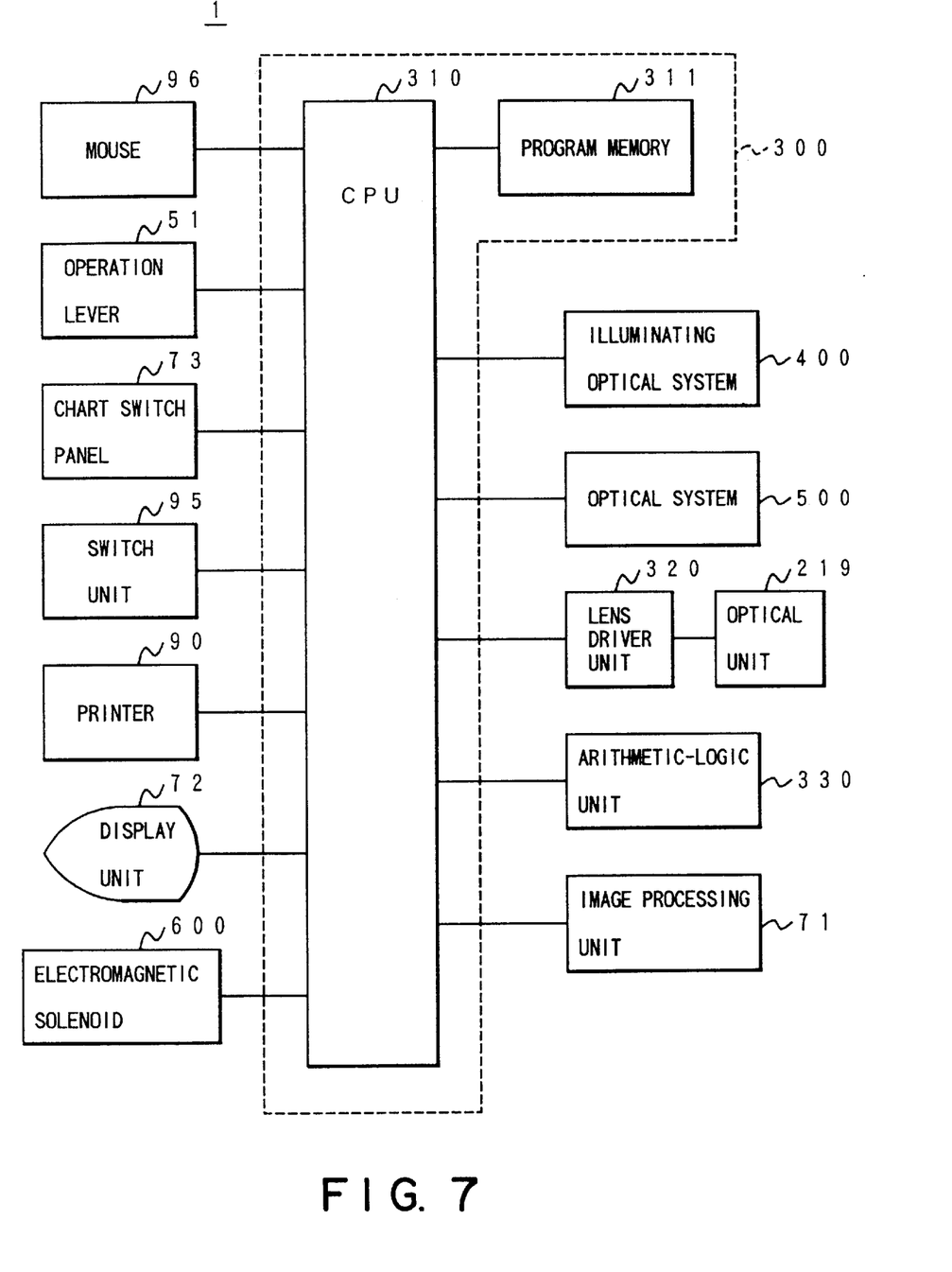
FIG. 7 shows a block diagram of a control system of the objective refraction measuring apparatus according to the embodiment.

The structure of the control unit for the objective refraction measuring apparatus 1 will now be described with reference to FIG. 7.

The objective refraction measuring apparatus 1 has a control unit 300 composed of a CPU (central processing unit) for controlling the overall apparatus and a program memory 311 for storing the control program. Connected to the CPU 310 are the operation lever 51, the display unit 72, the chart switch panel 73, the printer 90, the switch unit 95, the mouse 96, and the electromagnetic solenoid 600.

The illuminating optical system 400 and the optical system 500 are controlled by the CPU 310. Also, the lens driver unit 320 for moving the optical unit 219 is drive-controlled by the CPU 310.

Further, connected to the CPU 310 is an arithmetic-logic unit 330 for calculating the subjective measurement values, the objective measurement values and the defocus degree of the defocus confirmation pattern, which are measured by the respective optical systems, based upon the results processed through the light receiving element 5 and the image processing unit 71.

The drive control of the electromagnetic solenoid 600 is performed by the CPU 310, so that the diaphragm 503 is interposed in the optical path of the objective refraction measuring system in accordance with the operation of the separate chart switch 74e.

The operation of the objective refraction measuring apparatus 1 will now be described. First of all, the case where the subjective eye inspection is carried out by the person to be examined by himself or herself will now be described.

Under the condition that the power source switch 93 of the objective refraction measuring apparatus 1 is turned on, the examiner sets the subjective eye inspection mode using the switch unit 95 and then depresses the separate chart switch 74e of the switch panel 73 to interpose the separate chart 501 into the optical path of the eye fixation/subjective measuring system 3.

Under this condition, the visible light having the wavelength of from 400 to 700 nm emitted by the light source 30 of the eye fixation/subjective measuring system 3 is collected by the condenser lens 31 and then illuminated on the separate chart 501 in the chart plate 32a.

The light passed through the marks 501a and 501b of the separate chart 501 is formed into a pair of rays of light in the separate condition by the respective prisms 502a and 502b of the split prism 502. The pair of rays of light are merged into the measuring optical system 21 of the objective refractive measuring system 2 through the projection lens 35, the mirror 36 and the mirror 217, pass the filter 215 through the focusing lens 216, and introduced into the mirror 212 through the mirror 214 and the relay lens 213. The pair of rays of light are diaphragmed by the diaphragm 503 having the pair of through holes 503a and 503b which function as the red filter and the green filter arranged corresponding to the pair of separately arranged marks 501a and 501b which constitute the separate chart 501 shown in FIG. 6 and then are introduced into the variable cross cylinder 37.

The pair of rays of light passed through the variable cross cylinder 37 is reflected by the mirror 38 and the mirror 111, projected to the eye E to be examined by the objective lens 110 and observed by the eye E to be examined.

In this case, when the person to be examined depresses a plus button or a minus button of the mouse 96 by his or her finger, the lens driver unit 320 causes the optical unit 219 to move on the basis of the control of the CPU 310 in response to the signal from the mouse 96, so that the position of the focusing lens 216 is shifted in the plus direction or the minus direction along the optical axis, as shown in FIG. 6.

Figure 8A:
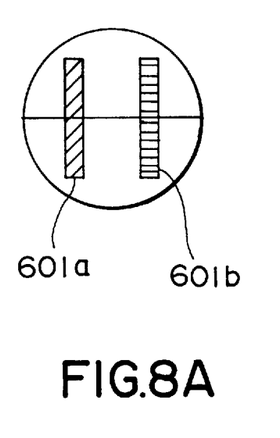
FIGS. 8A to 8C show the observation condition of the separate charts to the eye to be examined in the objective refraction measuring apparatus according to the embodiment.
Figure 8B:
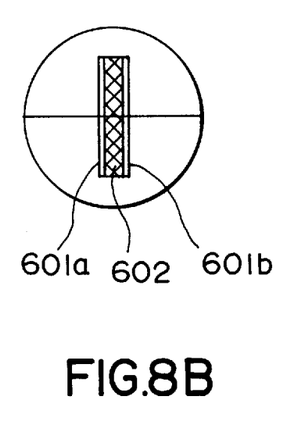
Figure 8C:
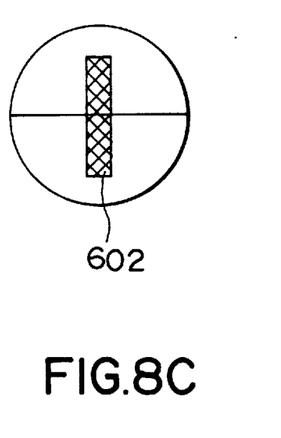

As a result, as shown in FIGS. 8A to 8C, the images of the pair of separately arranged marks 501a and 501b observed by the eye E to be examined are changed from the condition that the images 601a and 601b of the marks 501a and 501b are separated right and left to the condition that the images are partially overlapped with each other or completely identical with each other. In FIGS. 8A to 8C, the image 601a of the mark 501a is indicated by the oblique lines representing the red color, and the image 601b of the mark 501b is indicated by the horizontal lines representing the green color.

As shown in FIG. 8C, under the condition that the images of the marks 501a and 501b are identical with each other, it means that the marks 501a and 501b are in conjugative relation with the fundus ER of the eye E to be examined. Thus, the eye E observes a white color image 602 (indicated by cross oblique lines) where the green color and the red color are mixed with each other. In this case, the eye E to be examined may be observe the far-sight position (zero diopter in an emmetropia eye) at which the adjustment force does not work in the eye E.

Also, when the position of the focusing lens 216 is changed in the minus direction along the optical axis by the operation of the mouse 96, the limit position where the images 601a and 601b of the marks 501a and 501b are displaced to both sides of the image 602, as shown in FIG. 8B, means the limit for the adjustment force (several diopters) of the eye E to be examined, i.e., the near-sight position shifted by several diopters from the subjective measurement value obtained in the far-sight position.

Thus, the conditions of eye E to be examined for the far-sight position and the near-sight position in the above conditions are automatically measured by the eye fixation/subjective measuring system 3. A spherical degree S, a cylindrical degree C and an axis angle A are obtained by the operation of the image processing unit 71 and the arithmetic-logic unit 330 and these values are displayed on the display unit 72.

As described above, the person to be examined may perform the subjective measurement of the eye E to be examined by himself or herself while observing the images 601a and 601b and the image 602.

The case where both objective and subjective measurements are performed by the objective refraction measuring apparatus 1 will now be described. First of all, the objective measurement mode is set by the chart switch panel 73 and then the objective measurement of the eye E received by the jaw receiver base 82 is performed.

The objective refractive measuring system 2 of the optical system 500 measures the eye E to be examined in an objective manner on the basis of the above-described optical arrangement. The objective measurement values of the objective refractive measuring system 2 are processed by the light receiving element 5, the image processing unit 71 and the arithmetic-logic unit 330. Thus, the objective measurement values including the spherical degree S, the cylindrical degree C and the axis angle A of the eye E to be examined are obtained.

The CPU 310 automatically switches over the objective refraction measuring apparatus 1 to the subjective measurement mode on the basis of the obtained objective measurement values and controls the lens driver unit 320 to move the focusing lens 216 so that the separate chart 501 of the eye fixation/subjective measuring system 3 is located in a predetermined position relative to the far-sight position of the eye E to be examined. With such an operation, it is possible to perform both the objective measurement and the subjective measurement of the eye E to be examined with the objective refraction measuring apparatus 1, and at the same time to measure the addition power of the eye E to be examined.

In addition to the above case, it is possible to set the separate chart 501 to the near-sight position of the eye E to be examined on the basis of the subjective measurement values of the far-sight position of the eye E obtained by the eye fixation/subjective measurement system 3 and the arithmetic-logic unit 330 in the subjective measurement mode. Thus, it is possible to automatically measure the addition power of the eye E to be examined.

The thus obtained objective measurement values and subjective measurement values of the eye E are displayed on the display unit 72 as shown in FIG. 9. The examining person may compare and review the results of the objective and subjective measurements.

The case where the examining person confirms the observation condition of the person to be examined by the display unit 72 will now be explained.

The objective refractive measuring system 2 of the optical system 500 in the objective refraction measuring apparatus 1 measures the refractive power of the eye E to be examined in the objective manner. Also, the eye fixation/subjective measuring system 3 measures the refractive power of the eye E to be examined in the subjective manner by the projection of the separate chart 501 for the eye E. Further, the pattern projection system 20 in the objective refractive measuring system 2 projects, to the fundus ER of the eye E, the ring pattern 203 which also serves as a defocus confirmation pattern.

The arithmetic-logic unit 330 obtains the objective measurement values and the subjective measurement values of the eye E to be examined on the basis of the measurement results through the objective refractive measuring system 2 and the eye fixation/subjective measuring system 3 and may confirm the degree of the defocus condition of the reflective image on the basis of the reflective image of the ring pattern 203 to the eye E by the pattern projection system 20.

Figure 10:
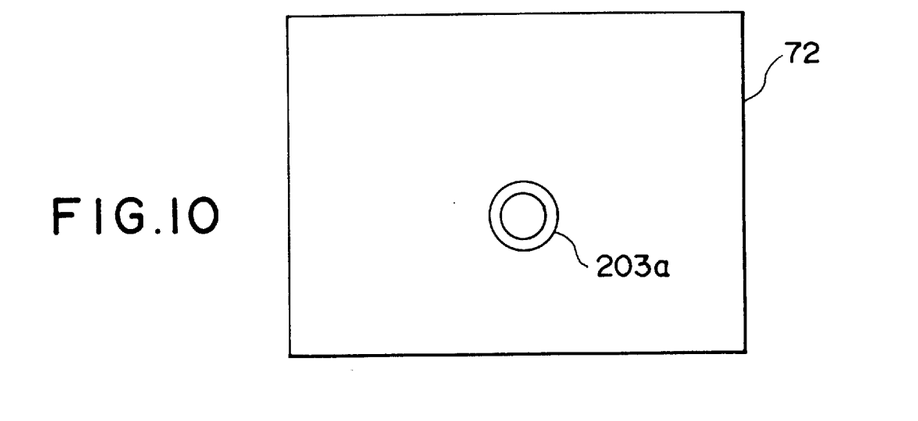
FIGS. 10 and 11 show a display condition of a defocus confirmation image in the objective refraction measuring apparatus according to the embodiment.
Figure 11:
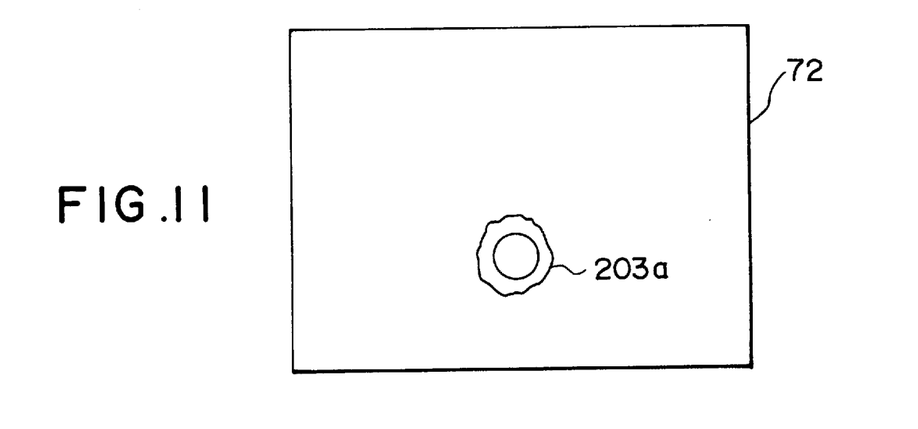

The display unit 72 displays the subjective measurement values of the eye E obtained by the eye fixation/subjective measuring system 3 and the arithmetic-logic unit 330 in the subjective measurement mode and at the same time displays the defocus confirmation image 203a corresponding to the defocus degree of the ring pattern 203 obtained by the arithmetic-logic unit 330 as shown in FIGS. 10 and 11.

Namely, when the outline of the defocus confirmation image 203a is clear as shown in FIG. 10, the examining person may confirm the condition that the separate chart 501 or the like is clearly observed by the person to be examined in the subjective measurement mode. Also, when the outline of the defocus confirmation image 203a is not clear as shown in FIG. 11, the examining person may confirm the condition that the separate chart 501 or the like may be observed by the person to be examined in a blurred manner in the subjective measurement mode.

Thus, the examining person may confirm the degree of defocus of the chart which the person to be examined is observing by using the display unit 72.

In addition to the above-described projection of the ring pattern 203 to the eye E to be examined, it is possible to confirm the degree of defocus of the separate chart 501 which the person to be examined is observing, by projecting the separate chart 501 to the eye E, receiving the reflective image thereof with the light receiving element 5 to perform the image processing and displaying the processing result on the display unit 72. Also, it is possible to confirm the degree of defocus of the chart which the person to be examined is observing, by preparing a plurality of frame memories (not shown), storing the defocus confirmation image 203a according to the degree of defocus of the ring pattern 203 and displaying the image on the display unit 72.

Also, in addition to the above, it is possible to confirm the degree of defocus of the chart which the person to be examined is observing, by operation of the examining person using the mouse 96 and making questions to the person to be examined while shifting the focusing lens 216.

It is possible to perform the following steps. The message of "alignment OK" is displayed on the display unit 72 together with the display of the alignment circle AR by the observation/alignment system 4. Only when the brightness point GR generated with the light emission of the focusing/positioning light source 41 of the observation/alignment system 4 is included into the alignment circle AR, the alignment is completed and the message of "alignment OK" is blinked. Only in this case, it is possible to enable the objective measurement or the subjective measurement or enable the print operation of the printer 90.

Also, in the subjective measurement using the separate chart 501, when the position of the focusing lens 216 is initialized to the more plus direction side shown in FIG. 6 than the position of the zero diopter of the eye E by the lens driver unit 320 and is shifted toward the minus direction side from the initialized position under the control of the CPU 310, it is possible to start certainly the positive subjective measurement without working the adjustment force to the eye E to be examined.

It is possible to change and modify the present invention within the scope of the claims in addition to the above described specific embodiment.

The present invention described in detail brings about the following advantages.

According to the present invention, it is possible to provide an objective refraction measuring apparatus in which the person to be examined may perform the subjective measurement of his or her eye to be examined by himself or herself.

According to the invention, it is also possible to provide an objective refraction measuring apparatus in which the separate chart and the diaphragm cooperate with each other whereby the person to be examined may rapidly perform the subjective measurement of his or her eye to be examined by himself or herself.

According to the present invention, it is possible to provide an objective refraction measuring apparatus in which red and green color images are projected to the eye to be examined by himself or herself to quickly perform the subjective measurement.

What is claimed is:

1. An objective refraction measuring apparatus for measuring a refractive power of an eye to be examined in an objective manner, comprising:

a separate chart having a pair of charts arranged separately;

an optical system for projecting the separate chart to the eye through a focusing lens and a diaphragm having a pair of holes arranged corresponding the pair of charts;

moving means for moving the focusing lens along an optical axis direction to perform a focusing operation to the eye; and means for measuring the eye in a subjective manner while the projection images of the pair of charts to the eye are obtained in an identical condition or a non-identical condition by moving the focusing lens by the moving means.

2. The apparatus according to claim 1 wherein the diaphragm is interposed in an optical path of the optical system in accordance with the separate chart.

3. The apparatus according to claim 1 wherein the pair of holes of the diaphragm have a red slit and a green slit, respectively.

4. The apparatus of claim 1 wherein the moving means moves the focusing lens in accordance with an objective measurement value obtained from an objective measurement such that the separate chart is set to a desired position in relation to a far-sight position of the eye.

5. The apparatus according to claim 1 wherein the subjective measurement of the eye can be performed by a person that the eye is examined.

* * * * *

UNITED STATES PATENT AND TRADEMARK OFFICE
CERTIFICATE OF CORRECTION

PATENT NO. : 5,844,660
DATED : Dec. 1, 1998
INVENTOR(S) : Saeko Uchida, et al.

It is certified that error appears in the above-indentified patent and that said Letters Patent is hereby corrected as shown below:

On the cover page, Line [73], should also list --Kabushiki Kaisha, Miki, Tokyo, Japan--.

Signed and Sealed this

Fifth Day of October, 1999

Attest:

Q. TODD DICKINSON

Attesting Officer

Acting Commissioner of Patents and Trademarks